United States Patent [19]
Colón et al.

[11] Patent Number: 5,480,525
[45] Date of Patent: Jan. 2, 1996

[54] MACHINE-ACCESSIBLE ELECTROCHEMICAL DETECTOR FOR CAPILLARY ELECTROPHORESIS

[75] Inventors: Luis A. Colón, Amherst, N.Y.; Rajeev Dadoo, Stanford, Calif.; William H. Whitted, Palo Alto, Calif.; Richard N. Zare, Stanford, Calif.; Andrew G. Ewing; Sandra S. Ferris, both of State College, Pa.; Jennifer U. Woelker, Madison, Wis.

[73] Assignee: The Board of Trustees of the Leland Stanford Junior University, Palo Alto, Calif.

[21] Appl. No.: 235,299

[22] Filed: Apr. 29, 1994

[51] Int. Cl.$^6$ ............................. B01D 61/42; B01D 61/46
[52] U.S. Cl. .................................... 204/180.1; 204/299 R
[58] Field of Search ............................. 204/299 R, 180.1

[56] References Cited

U.S. PATENT DOCUMENTS

| | | | |
|---|---|---|---|
| 5,126,023 | 6/1992 | Huang et al. | 204/180.1 |
| 5,223,114 | 6/1993 | Zare et al. | 204/299 R |

FOREIGN PATENT DOCUMENTS

| | | |
|---|---|---|
| 581983 | 2/1994 | European Pat. Off. |
| 2113837 | 4/1986 | Germany |

OTHER PUBLICATIONS

Wallingford et al., Dept. of Chemistry, Penn State, "Capillary Zone Electrophoresis with Electrochemical Detection", 1987 American Chemical Society, Anal. Chemistry, vol. 59, Anal. Chemistry, vol. 59, No. 14, Jul. 15, 1987, pp. 1762–1766.

Huang et al., Dept. of Chemistry, Stanford University, "On–Column Conductivity Detector for Capillary Zone Electrophoresis", 1987 American Chemical Society, Anal. Chemistry, vol. 59, No. 23, Dec. 1, 1987, pp. 2747–2749.

Huang et al., Dept. of Chemistry, Stanford Univ., "Effect of Electrolyte and Sample Concentration on the Relationship Between Sensitivity and Resolution in Capillary Zone Electrophoresis using Conductivity Detection", 1989 Elsevier Science Pubs. B.V. Amsterdam, Jour. of Chromatography, vol. 480, pp. 285–288. 1989 (No Month).

Huang et al., Dept. of Chemistry, Stanford Univ. "Quantitative Analysis of Low Molecular Weight Carboxylic Acids by Capillary Zone Electrophoresis/Conductivity Detection", Amer. Chemical Society, Anal. Chemistry, vol. 61, No. 7, Apr. 1, 1989, pp. 766.770.

Kuhr, Dept. of Chemistry, Univ. of Calif. Riverside, "Capillary Electrophoresis", Amer. Chemistry Society, Anal. Chemistry, vol. 62, No. 12, Jun. 15, 1990, pp. 403R–414R.

Foret et al., Institute of Analytical Chemistry, Czechoslovak Academy of Sciences, Brno, "On–line fiber optic UV detection cell and conductivity cell for capillary zone electrophoresis", VCH Verlagsgesellschaft mbH, D–6940 Weinheim, 1986, Electrophoresis 1986, vol. 7, pp. 430–432. (No Month).

Huang et al., Dept. of Chemistry, Stanford University, "Use of an On–Column Frit in Capillary Zone Electrophoresis: Sample Collection", 1990 American Chemical Society, Anal. Chemistry, vol. 62, No. 5, Mar. 1, 1990, pp. 443–446.

Huang et al., Dept. of Chemistry, Stanford University, Sandra Sloss and Andrew G. Ewing, Dept. of Chemistry, Penn State University, "End–Column Detection for for Capillary Zone Electrophoresis", 1991 American Chemical (List continued on next page.)

*Primary Examiner*—John Niebling
*Assistant Examiner*—Edna Wong
*Attorney, Agent, or Firm*—Majestic, Parsons, Siebert & Hsue

[57] ABSTRACT

End-column detectors are provided in which either a sensing microelectrode or optical fiber is placed at the end of the separation capillary. Additionally, an alignment apparatus is provided to facilitate the manual or automated positioning of either type of sensing device relative to the end of the separation capillary. The invention provides detectors that are sensitive, reliable, and easy to construct and to operate.

38 Claims, 4 Drawing Sheets

OTHER PUBLICATIONS

Society, Anal. Chemistry, vol. 63, No. 2, Jan. 15, 1991, pp. 189–192.

Huang et al., Dept. of Chemistry, Stanford Univ., "Current–Monitoring Method for Measuring the Electroosmotic Flow Rate in Capillary Zone Electrophoresis", 1988 American Chemical Society, Anal. Chemistry, vol. 63, pp. 1838–1840. (No Month).

Abdel–Latif et al., Dept. of Chemistry, Univ. of New Orleans, "Fiber–Optic Sensor for the Determination of Glucose Using Micellar Enhanced Chemiluminescence of the Peroxyoxalae Reaction", 1988 American Chemical Society, Anal. Chemistry, vol. 60, No. 24, Dec. 15, 1988, pp. 2674–2679.

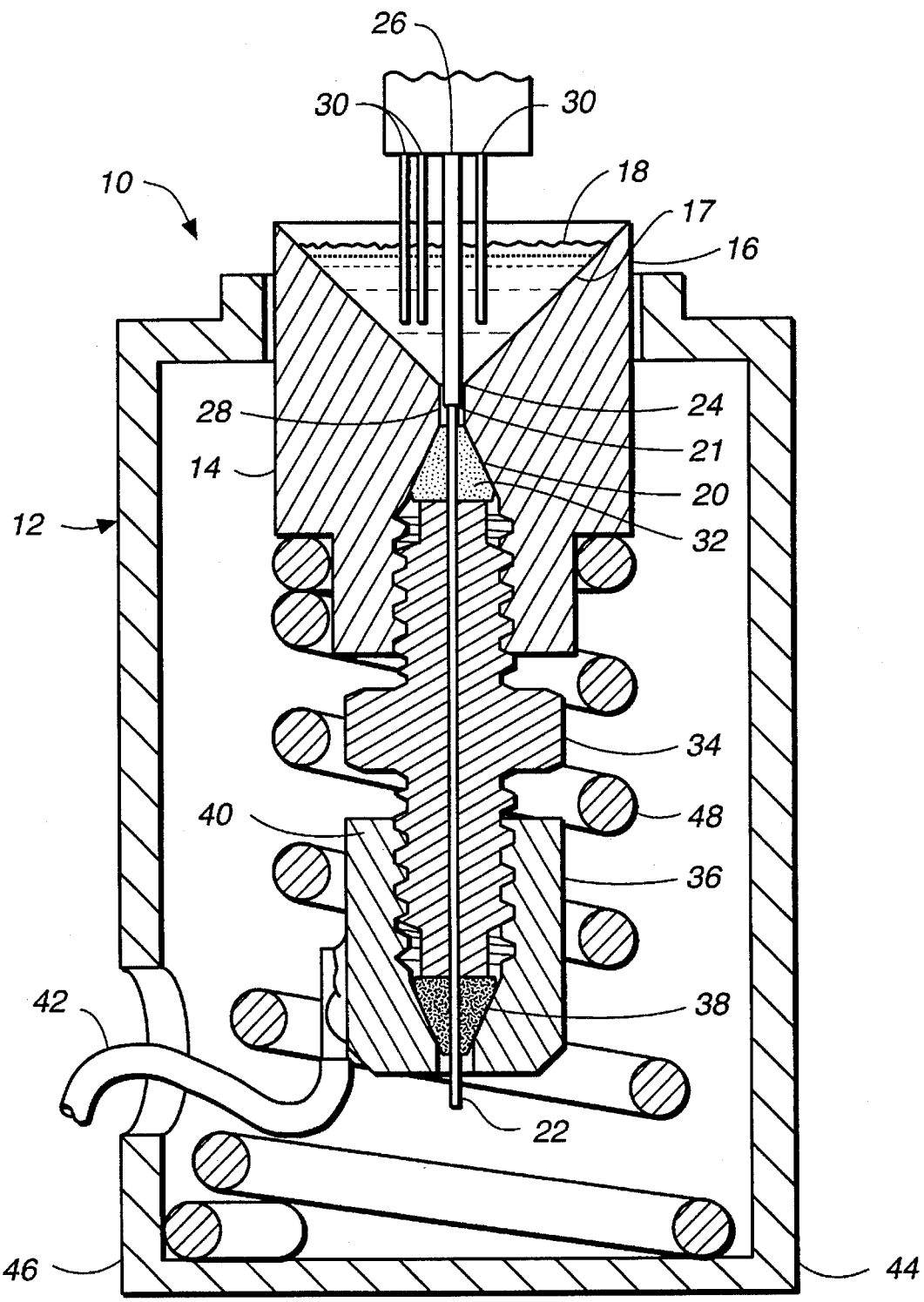
FIG._1A

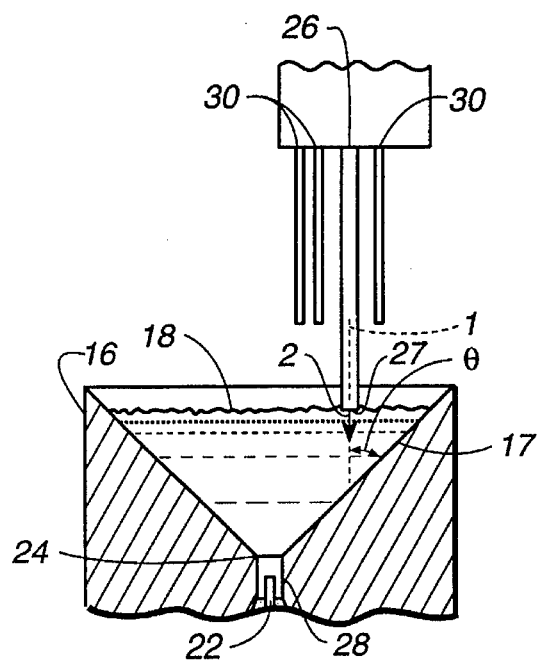
FIG._1B
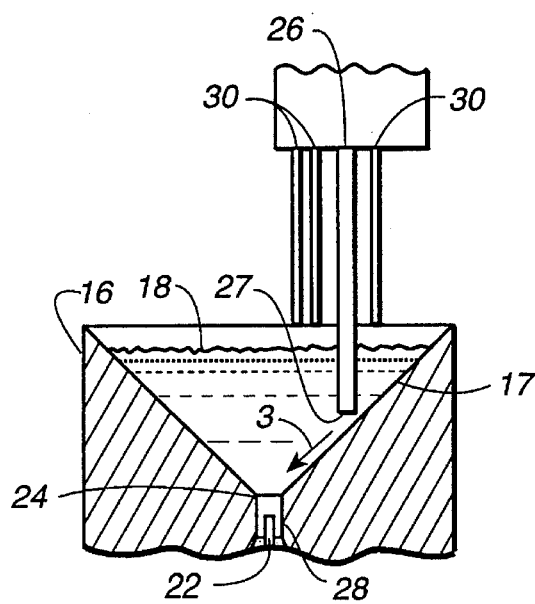
FIG._1C
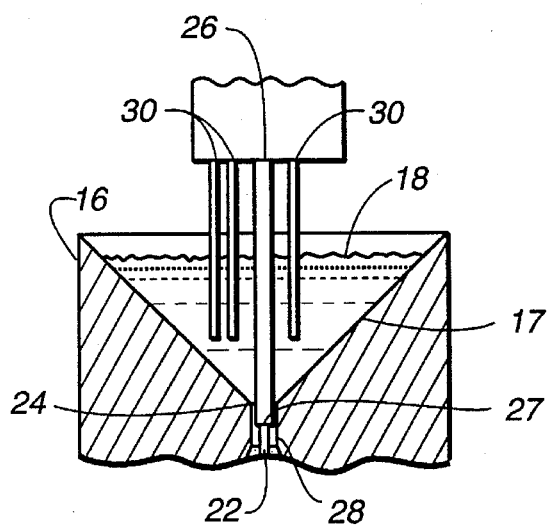
FIG._1D
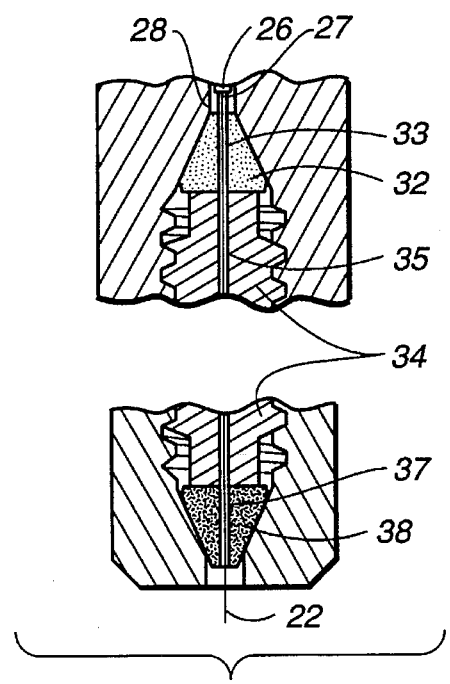
FIG._1E

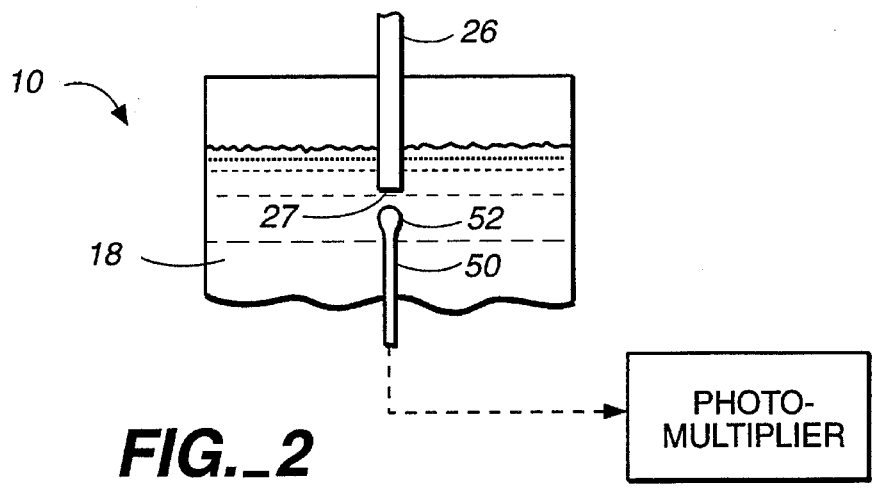
FIG._2
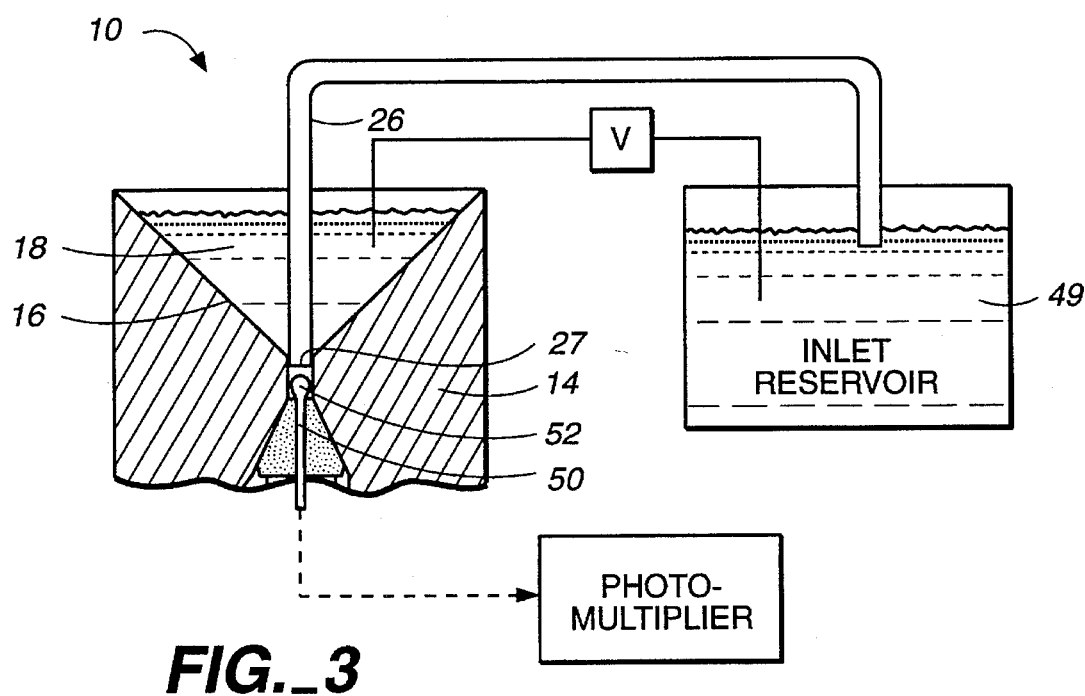
FIG._3
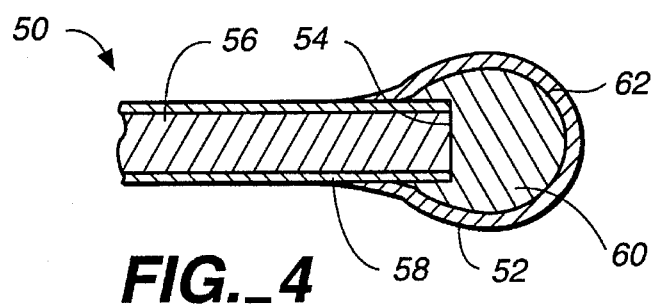
FIG._4

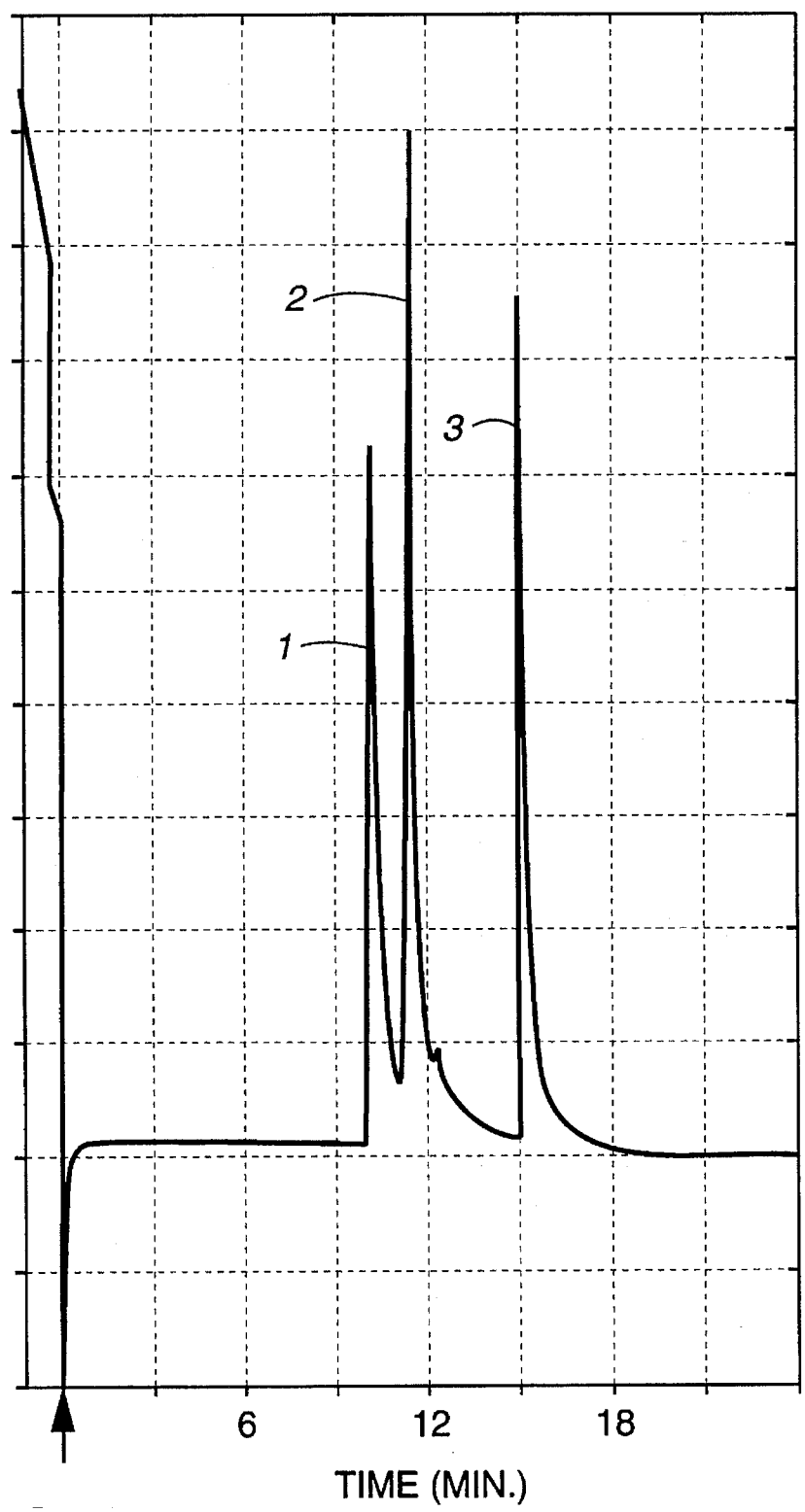
FIG._5

MACHINE-ACCESSIBLE ELECTROCHEMICAL DETECTOR FOR CAPILLARY ELECTROPHORESIS

FIELD OF THE INVENTION

The invention relates generally to capillary separation devices and particularly to an improved detection device for capillary electrophoresis. More specifically, the present invention relates to an alignment device for a detector used in capillary electrophoresis and methods of using same.

BACKGROUND OF THE INVENTION

Zone electrophoresis in capillaries has become an important technique in the repertoire of liquid-phase separations. See Jorgenson et al., *Science* 242 (1983); Gordon et al., *Science* 242 (1988), 224–228; Ewing et al., *Anal. Chem.* 61 (1989), 292A–303A; Wallingford et al., *Advances in Chromatography* 29 (1989), 1–76; and Kuhr, *Anal. Chem.* 62 (1990), 403R–414R. Capillary electrophoresis has been used for separations of small and large molecules and comprises several subtechniques including capillary zone electrophoresis (CZE), capillary gel electrophoresis, micellar electrokinetic capillary chromatography, and capillary isoelectric focusing.

A major aspect of CZE in need of new development is detection; specifically, there is a critical need for detectors capable of responding to the small quantity of sample component in the effective detection volume. Detection schemes developed to date include direct and indirect UV absorption (Hjerten, *J. Chromatogr.* 347 (1985), 191–198 and Hjerten et al., *J. Chromatogr.* 3 (1987), 47–61), fluorescence (Jorgenson et al., *Anal. Chem.* 53 (1981), 1298–1302) and Kuhr et al., *Anal. Chem.* 60 (1988), 2642–2644) and radioisotope (Pentoney et al., *Anal. Chem.* 61 (1989), 16421647), as well as mass spectrometric (Smith et al., *Anal. Chem.* 60 (1988), 436–441; Lee et al., *Biomed. Environ. Mass Spectrom.* 18 (1989), 844–850; Moseley et al., *Chromatogr.* 480 (1989), 197–210; and Caprioli et al., *J. Chromatogr.* 480 (1989), 247–258) and electrometric (Mikkers et al., *J. Chromatogr.* 169 (1979), 11–20; Huang et al., *Anal. Chem.* 59 (1987), 2747–2749; and Wallingford et al., *Anal. Chem.* 59 (1987), 1762–1766) detectors.

However, because CZE employs extremely high potential fields (typically 300 V/cm) to achieve highly efficient separations, detection schemes for CZE are designed to prevent the high potentials used from interfering with the detection process. For example, existing electrical and electrochemical detectors for CZE use elaborate on-column and post-column detection schemes to prevent such interference. One scheme involves construction of 40 μm-diameter holes in the capillary using a laser. Thereafter, small platinum wire electrodes are placed in these holes to carry out on-column conductivity detection. It has been demonstrated that the exact placement of these electrodes on opposite sides of the capillary is critical to minimize noise associated with the high potential field used for separation (Huang et al., *Anal. Chem.* 59 (1987), 2747–2749). In U.S. patent application Ser. No. 443,059, filed Nov. 28, 1989 and now abandoned, by Zare et al. (continued in Ser. No. 744,642, filed on Aug. 8, 1991 and issued as U.S. Pat. No. 5,223,114 on Jun. 29, 1993), on-column conductivity detectors were disclosed wherein on-column sensing electrodes are located contiguous with the exit of the separation microcolumn. The sensing electrodes must be carefully aligned and an isolation transformer must be used in measuring the conductance (Huang et al., *Anal. Chem.* 59 (1987), 2747–2749; and Everaerts et al., Isotachophoresis, *Journal of Chromatography Library* 6, Elsevier: Amsterdam, 1976).

Turning to another detection scheme, Huang et al. recently reported the use of an end-column structure for conductimetric and amperometric detection for CZE in which the sensing electrode is placed at the outlet of the fused-silica capillary (Huang et al., *Anal. Chem.* 63 (1991), 189–192). While such end-column detectors (also described in U.S. Pat. No. 5,126,023, issued on Jun. 30, 1992 to Huang et al.) demonstrate sensitivities that approach those of previous on-column conductivity detectors, the end-column structures require carefully matched microplumbing in which the analytical capillary is placed inside a second capillary that has an inside diameter slightly larger than the outside diameter of the analytical capillary. For conductimetric detection, epoxy is used in such structures to help maintain structural integrity of the electrode. However, if the epoxy becomes exposed to the electrolyte, it may affect measurements.

Therefore, although good results have been obtained with current detection systems, these systems are limited by their need for painstaking alignment and precise manipulation in situating the various sensing electrodes relative to the separation column. Such limitations result in structures that are difficult to fabricate, expensive and, often times, unreliable. These limitations are especially problematic in electrochemical detectors which are easily fouled during normal use and require frequent cleaning or changing of electrodes. After an electrode is changed, the repeatability of results is very questionable. These problems have limited the routine application of both on-column and post-column modes of electrochemical detection in CZE. See Ewing et al., *Anal. Chem.* 61 (1989), 292A–303A; Kuhr, *Anal. Chem.* 62 (1990), 403R–414R; Huang et al., *Anal. Chem.* 61 (1989), 766–770; Huang et al., *J. Chromatogr.* 425 (1988), 385–390; Huang et al., *J. Chromatogr.* 480 (1989), 285–288; Wallingford et al., *Anal. Chem.* 60 (1988), 1972–1975; Wallingford et al., *Anal. Chem.* 60 (1988), 258–263; Wallingford et al., *J. Chromatogr.* 441 (1988), 299–309; and Wallingford et al., *Anal. Chem.* 61 (1989), 98–100. Additionally, the alignment limitation has precluded the use of existing detectors with automated systems in which the capillary column is automatically connected to and disconnected from the detector. There is a further detection scheme that has yet to be employed in CZE, namely, fiber optic detection (i.e., with chemiluminescence). For example, the use of fiber optics for chemical analysis has been described by Abdel-Latif et al., *Anal. Chem.* 60 (1988), 2671–2674. It would be useful to develop a fiber optic detection system for CZE such that a minimally dimensioned optical fiber could be used to accurately detect analyte concentration at the end of the capillary column.

SUMMARY OF THE INVENTION

It is an object of the present invention to provide detection devices for use in capillary separation techniques which eliminate the alignment problems associated with current detection devices. Further, it is an object of the present invention to provide such detection devices that are easy and relatively inexpensive to construct and convenient to manufacture using mass production methods.

It is another object of the present invention to provide detection devices for use in capillary separation techniques which facilitate the use of a variety of sensing electrodes and the changing of such electrodes.

Yet another object of the present invention is to provide detection devices for use in capillary separation techniques which facilitate their automated and repeated connection to and disconnection from the separation column.

Still another object of the present invention is to provide detection devices for use in capillary separation techniques which eliminate the use of epoxy near the measurement electrode and thus, eliminate detection problems associated with the contact of epoxy and electrolyte and/or the contact of epoxy and the measurement electrode.

It is a further object of the present invention to provide an optical detection device for use in capillary separation techniques which comprises an optical fiber as opposed to more conventional measurement means.

These and other objects are achieved by the present invention which generally provides an apparatus for aligning a detection electrode with a capillary column which includes an alignment device and a measurement electrode positioned therein (without the use of epoxy). The alignment device includes a vessel for containing an electrolytic fluid which has an opening and a substantially sloped portion. In a preferred embodiment, the vessel is substantially funnel-shaped and has the opening at its narrowest end. The vessel is configured such that its sloped portion is at an acute angle to a direction in which an end of the capillary column is oriented. When the alignment apparatus is brought into contact with the separation capillary, the sloped vessel serves to direct the end of the separation capillary along its slope and toward the vessel opening and thereby, to position the end of the separation capillary relative to the opening. In this manner, the alignment apparatus aligns the separation capillary with the measurement electrode which is positioned within the alignment apparatus and relative to the vessel opening.

Thus, the alignment apparatus of the present invention eliminates the significant alignment problems of existing detection systems. Further, the simplified method of using the alignment apparatus lends itself to automation in that the positioning of the apparatus in operable communication with the capillary column can be simply mechanized to facilitate the alignment of the capillary column and the measurement electrode. Because the alignment device of the present invention is simply configured, it can be easily and inexpensively manufactured using mass production methods. It is also designed for the expedient placement, removal, replacement or changing of the measurement electrode and thus, facilitates both the quick change of electrodes and the use of electrodes of various construction or properties. In fact, according to one embodiment of the present invention, the measurement electrode can be dispensed with and replaced by an optical fiber of an optical detection system.

Additional objects, advantages and features of the various aspects of the present invention will become apparent from the following description of its preferred embodiments, which description should be taken in conjunction with the accompanying drawings.

BRIEF DESCRIPTION OF THE DRAWINGS

FIG. 1a illustrates an end-column electrochemical detection apparatus according to the present invention.

FIGS. 1b–1d schematically illustrate, in cut-away, the alignment of a measurement detector with a capillary column according to the present invention.

FIG. 1e illustrates, in cut-away, alternative embodiments of an adaptive sleeve component in a central portion of an end-column electrochemical detection apparatus according to an embodiment of the present invention.

FIG. 2 schematically illustrates, in cut-away, an end-column optical detection apparatus according to the present invention.

FIG. 3 schematically illustrates, in cut away, an end-column optical detection apparatus according to the present invention.

FIG. 4 illustrates, in cut-away, an optical fiber component of an optical detection apparatus according to the present invention.

FIG. 5 is an electropherogram obtained with end-column amperometric detection.

DESCRIPTION OF A PREFERRED EMBODIMENT

FIG. 1a illustrates a capillary electrophoresis apparatus (10) which includes a capillary column (26), at least one ancillary electrode (30), a conductive electrolyte fluid (18) and an end-column electrochemical detection apparatus (12). The central part of the detection apparatus (12) is alignment device (14), which generally comprises a vessel or funnel (16) for containing electrolytic fluid (18) and a detector-retaining portion (20) for positioning measurement detector (22) relative to vessel (16).

Preferably, vessel (16) is electrically non-conductive. Vessel (16) has a substantially sloped portion (17) and an opening (24). Preferably, sloped portion (17) is substantially funnel-shaped; however, sloped portion (17) may be flat, curved, wedged or otherwise shaped. The opening (24) is preferably disposed near the end of the sloped portion (17) of vessel (16), although other appropriate positionings of opening (24) relative to sloped portion (17) are contemplated. As shown in FIG. 1a, disposed between vessel opening (24) and retaining portion (20) is a narrow-bore hole (28), which is contiguously aligned with retaining portion (20).

A preferred method of aligning capillary column (26) of electrophoresis apparatus (10) with end-column detection apparatus (12) includes placing alignment device (14) adjacent an end (27) of capillary column (26), as schematically shown in FIGS. 1b–1d.

FIG. 1b shows an elongated capillary column (26) oriented along a direction (represented by dotted line 1) and being moved (represented by arrow 2) toward sloped portion (17) which is at an acute angle (θ) relative to the direction of column (26). Directions for column (26) other than the direction shown in FIG. 1b and orientations of sloped portion (17) other than that shown in FIG. 1b are contemplated, provided angle (θ) is acute. Additionally, either capillary column (26) or sloped portion (17) may be moved relative to the other, or both may be moved relative to each other, to achieve the desired column-detector alignment of FIG. 1d.

As shown in FIG. 1c, once contact is made between end (27) of capillary column (26) and sloped portion (17), sloped portion (17) directs (represented by arrow 3) end (27) of capillary column (26) along the slope of sloped portion (17), whatever the actual shape of that slope, toward vessel opening (24) and narrow-bore hole (28). In this manner, end (27) of capillary column (26) is positioned adjacent measurement detector (22), appropriately aligned for end-column detection, as shown in FIG. 1d. In the event capillary column (26) is directed straight-on toward vessel opening (24), contact between capillary column (26) and sloped portion (17) will not be necessary to achieve the alignment of FIG. 1d.

In a CZE process, capillary column (26) is filled with a fluid support electrolyte which elutes from end (27) of capillary (26). Capillary (26) may be fixed in place and some or all of ancillary electrodes (30) may be mounted in vessel (16). Once fluid-filled capillary column (26) is positioned in alignment device (14), electrolyte fluid (18) contained in vessel (16) provides an electrical connection between capillary column (26) and ancillary electrodes (30).

Electrolyte fluid eluting from end (27) of aligned capillary column (26) passes measurement detector (22) and flows between narrow-bore hole (28) and the outer surface of capillary (26) into vessel (16). Thus, narrow-bore hole (28) has cross-sectional dimensions greater than that of end (27) of capillary (26). In a CZE system, narrow-bore hole (28) has a diameter preferably ranging from about 10 microns to about 200 microns greater than end (27) of capillary (26). Surrounding capillary (26), narrow-bore hole (28) also serves to constrain radial movement of capillary (26) therein.

Electrolyte fluid is prevented from leaking out of narrow-bore hole (28) by retaining portion (20) adjacent thereto. Retaining portion (20) also functions to retain measurement detector (22) within alignment device (14) and relative to narrow-bore hole (28), such that fluid eluting from end (27) of capillary (26) passes electrode (22) and is detected thereby. Retaining portion (20) substantially surrounds at least a portion of measurement detector (22). It includes a ferule (32), positioned adjacent narrow-bore hole (28), and a compression fitting (34), positioned adjacent ferule (32) at an end thereof opposite narrow-bore hole (28). Preferably, ferule (32) is electrically non-conductive.

Retaining portion (20) further includes a compression fitting (34), positioned adjacent ferule (32) at an end thereof opposite narrow-bore hole (28) and secured within alignment device (14). Compression fitting (34) is adapted to tightly secure ferule (32) against narrow-bore hole (28) to prevent substantially any leakage of fluid from narrow-bore hole (28). Preferably, compression fitting (34) is secured within alignment device (14) by screw-type male and female connection means. Disposed adjacent compression fitting (34) at an end thereof opposite ferule (32) is an electrically conductive portion (36). Conductive portion (36) substantially surrounds at least a portion of measurement detector (22) and is electrically connected thereto. Conductive portion (36) includes a ferule (38) which is preferably electrically conductive and a compression nut (40) which substantially surrounds ferule (38) and has a signal lead wire (42) connected thereto. Preferably, compression nut (40) is connected to compression fitting (34) by screw-type male and female connection means.

As illustrated in FIG. 1e, when a very small measurement detector is used in detection apparatus (12), one or more adaptive sleeves (33), (35) or (37) may be placed between the measurement detector (22) and ferule (32), compression fitting (34) or ferule (38), respectively. The use of such sleeves avoids the need for ferules and compression fittings having very small through holes. As shown in FIG. 1a, detection apparatus (12) includes a support portion (44) for alignment device (14) comprising a housing (46), which substantially surrounds alignment device (14), and a compression spring (48), which is disposed within housing (46) and between alignment device (14) and the base of housing (46). One end of compression spring (48) contacts alignment device (14), while an opposite end of compression spring (48) contacts the base of housing (46). When alignment device (14) is placed adjacent end (27) of capillary column (26), compression spring (48) (preferably, a very light spring) is either axially compressed in the direction of the base of housing (46) or axially decompressed in the direction of alignment device (14), depending on the length of capillary column (26). In this manner, support portion (44) axially adjusts to position alignment device (14) relative to capillary column (26), such that capillary column (26) is aligned with measurement detector (22) within alignment device (14).

In use, capillary column (26) is fixed in place and housing (46) is lifted to place vessel (16) of alignment device (14) adjacent end (27) of capillary column (26). Alternatively, capillary column (26) and any ancillary electrodes (30) may be moved relative to a movable or stationary alignment device (14). These placement methods and corresponding displacement methods may be automated. Once capillary column (26) is placed within alignment device (14), compression spring (48) axially adjusts to capillary column (26) so that the measurement detector (22) within alignment device (14) is securely positioned in a desired location relative to the outlet end of capillary column (26) for detection.

Detection apparatus (12) may be used with a variety of separation means that employ capillary columns. Additionally, it may be implemented as a conductivity, electrochemical, amperometric or other detection device requiring a small, accurately positioned measurement detector. Alternatively, the measurement detector may be a measurement electrode (22), as shown in FIG. 1a, or an optical measurement detector, as shown variously in FIG. 2, FIG. 3 and FIG. 4, described below, or any other appropriate measurement device.

FIG. 2 illustrates an electrophoresis apparatus (10) which includes a fiber optic detection apparatus. A tip (52) of an optical fiber (50) is placed relative to the end of capillary column (26) for the detection of analytes as they elute from capillary column (26) into electrolytic fluid (18). As fully described in relation to FIG. 4, optical fiber tip (52) is constructed such that it acts as an optical sensor. Communicating with tip (52), optical fiber (50) transmits a signal from tip (52) to a photomultiplier for detection.

FIG. 3 illustrates an electrophoresis apparatus (10) which includes a fiber optic detection apparatus according to an alternative embodiment of the present invention. Tip (52) of optical fiber (50) is aligned with end (27) of capillary column (26) by way of alignment device (14). Alignment device (14) is configured and operated substantially as described herein relative to FIG. 1a, with the exception that optical fiber (50) is used in place of measurement electrode (22). As is generally known in the art, electrophoresis apparatus (10) includes voltage source (V) which, similarly to capillary column (26), communicates with electrolytic fluid (49) in an inlet reservoir and electrolytic fluid (18) in vessel (16). An apparatus similar to FIG. 3 can be used for electrophoresis using column (26) of FIG. 1a.

FIG. 4 illustrates optical fiber (50) of FIG. 1a and FIG. 2 in greater detail. Optical fiber (50) is generally comprised of core (56), cladding (58), distal end (54) and a proximal end (not shown) opposite distal end (54). Adjacent distal end (54) is fluorescent material (60). While fluorescent material (60) is shown in FIG. 5 in the form of a bead, numerous alternative configurations are possible. Fluorescent material (60) is coated with reactive material (62) which is selected for its substantial reactivity with one or more of the analytes to be detected.

In operation, as analytes exit capillary column (26) they react with reactive material (62) on tip (52) of optical fiber (50). The reaction produces an intermediate which is capable of transferring energy to fluorescent material (60). Once energized, fluorescent material (60) emits light which is communicated to distal end (54) of optical fiber (50). The light generated is proportional to the concentration of analyte exiting column (26) and has a wavelength which is dependent on the type of fluorescent material used. The emitted light is then communicated via optical fiber (50) and its proximal end to the photomultiplier of a detection system for analyte detection. As is readily apparent, the optical fiber detection apparatuses of FIG. 2 and FIG. 3 are ideally suited to CZE systems because minimally dimensioned and flexible optical fibers can be used therein to accurately detect analytes eluting from a small diameter capillary column.

EXPERIMENTAL

Amperometric Detection. For amperometric measurements using the apparatus and method of the present invention, the cell (a 25 μm i.d.×370 μm o.d.× 57 cm length column) was filled with 50 Mm NaOH as supporting electrolyte. Injection of sugars was by electromigration (10 kV for 7 s). A separation voltage of 10 Kv was applied and a copper wire measurement electrode (200 μm in diameter) was used to detect sugar components. Detection was performed at 0.6 V vs. Ag/AgCl using a P/ACE 2000 from Beckman Instruments, Inc.

RESULTS

The electropherogram of FIG. 5 shows the separation of equimolar (approximately 0.5 Mm) concentrations of inositol (peak 1), sucrose (peak 2) and lyxose (peak 3). It is clear that sugars are readily separated using the apparatus and method of the present invention.

It is to be understood that while the invention has been described above in conjunction with preferred specific embodiments, the description and examples are intended to illustrate and not limit the scope of the invention, which is defined by the scope of the appended claims.

What is claimed is:

1. An apparatus for aligning a capillary column with a device for detecting one or more sample components in an eluent from the capillary column, the capillary column having an outlet end from which the eluent exits the capillary column, the outlet end oriented along a direction, comprising:

an alignment device including a vessel containing an electrolyte, said vessel having a sloped portion at an acute angle to the direction and an opening at or near the sloped portion, said sloped portion positioning the outlet end of the capillary column relative to said opening; and a detector positioned within said alignment device and spaced apart from the outlet end of the capillary column by a gap, said alignment device positioning said detector relative to the outlet end of the capillary column.

2. The apparatus of claim 1, wherein said sloped portion is funnel-shaped.

3. The apparatus of claim 1, wherein said vessel is an electrically non-conductive funnel.

4. The apparatus of claim 1, wherein said alignment device includes a narrow-bore hole disposed between said opening of said vessel and said detector, said narrow-bore hole surrounding the outlet end of the capillary column such that the outlet end of the capillary column is positioned adjacent said detector.

5. The apparatus of claim 4, wherein said narrow-bore hole has a diameter ranging from about 10 to about 200 microns greater than a diameter of the outlet end of the capillary column.

6. The apparatus of claim 4, wherein said narrow-bore hole has cross-sectional dimensions greater than the cross-sectional dimensions of the outlet end of the capillary column such that the eluent exiting the outlet end of the capillary column is allowed to pass by said detector, between said narrow-bore hole and an outer surface of the outlet end of the capillary column, and into said vessel.

7. The apparatus of claim 4, wherein said alignment device includes a retaining portion adjacent said narrow-bore hole, said retaining portion surrounding at least a portion of said detector and adapted to hold said detector within said alignment device.

8. The apparatus of claim 7, wherein said retaining portion includes an electrically non-conductive first ferule.

9. The apparatus of claim 8, wherein said retaining portion includes a sleeve disposed between said detector and said first ferule.

10. The apparatus of claim 8, wherein said retaining portion includes a compression fitting adjacent an end of said first ferule and said first ferule and said compression fitting cooperate to prevent substantially any leakage of electrolyte from said narrow-bore hole.

11. The apparatus of claim 10, further comprising an electrically conductive portion opposite said retaining portion and adjacent an end of said compression fitting, said conductive portion surrounding at least a portion of said detector and electrically connected thereto.

12. The apparatus of claim 11, wherein said conductive portion includes a second ferule.

13. The apparatus of claim 12, wherein said conductive portion includes a sleeve disposed between said detector and said second ferule.

14. The apparatus of claim 12, wherein said conductive portion includes a compression nut which surrounds said second ferule, said compression nut having a signal wire connected thereto.

15. The apparatus of claim 1, further comprising a support portion which supports said alignment device and axially adjusts to position said alignment device relative to the capillary column of a certain length such that the outlet end of the capillary column is positioned adjacent said detector.

16. The apparatus of claim 15, wherein said support portion includes a compression spring, having a first end which contacts said alignment device and a second end, and a housing which surrounds said compression spring and at least a portion of said alignment device and contacts said compression spring at the second end thereof.

17. The apparatus of claim 1, wherein said detector includes a measurement electrode.

18. The apparatus of claim 1, wherein said detector includes an optical fiber.

19. An apparatus for detecting one or more sample components in an eluent from a capillary column during capillary electrophoresis, comprising:

a capillary column having an outlet end from which the eluent exits the capillary column, the outlet end oriented along a direction;

at least one ancillary electrode;

an electrolyte in contact with the ancillary electrode for providing an electrical connection between said capillary column and the ancillary electrode;

an alignment device including an electrically non-conductive vessel containing the electrolyte, said vessel having a sloped portion at an acute angle to the direction and an opening at or near the sloped portion, said sloped portion positioning the outlet end of the capillary column relative to said opening; and a detector for detecting one or more sample components in the eluent, said detector positioned within said alignment device, said alignment device positioning said detector relative to the outlet end of the capillary column and dimensioned to allow the eluent to pass by said detector and into said vessel.

20. The apparatus of claim 19, wherein said ancillary electrode is mounted in said vessel.

21. The apparatus of claim 19, further comprising an electrically conductive portion surrounding and electrically connected to at least a portion of said detector.

22. The apparatus of claim 19, further comprising a support portion which supports said alignment device and axially adjusts to position said alignment device relative to the capillary column of a certain length such that the outlet end of the capillary column is positioned adjacent said detector.

23. The apparatus of claim 22, wherein said support portion includes a compression spring, having a first end which contacts said alignment device and a second end, and a housing which surrounds said compression spring and at least a portion of said alignment device and contacts said compression spring at the second end thereof.

24. The apparatus of claim 19, wherein said detector includes a measurement electrode.

25. The apparatus of claim 19, wherein said detector includes an optical fiber.

26. The apparatus of claim 19, wherein the detector is spaced apart from the outlet end of the capillary column by a gap.

27. A fiber optic device for detecting one or more sample components in an eluent from a capillary column, comprising:

a capillary column having an outlet end from which the eluent exits the capillary column;

a power source for applying an electrical field in a section of the column to cause separation of a sample;

an optical fiber for transmitting light energy between a distal end and a proximal end thereof, the distal end positioned to operably communicate with the outlet end of said capillary column and the proximal end positioned to operably communicate with a detector;

a tip adjacent the distal end of said optical fiber, said tip including a fluorescent material; and a reactive material overlying said fluorescent material for reacting with the eluent from the outlet end of the capillary column, thereby transmitting energy to the fluorescent material of said tip.

28. An apparatus for performing capillary electrophoresis, comprising:

a capillary column including an electrolyte therein and having an inlet and outlet end from which an eluent exits the capillary column, the outlet end being oriented along a direction;

a power source for applying an electrical field between the inlet and the outlet end to cause separation of a sample;

an alignment device including a vessel containing an electrolyte electrically communicating with the electrolyte in said capillary column, said vessel having a sloped portion at an acute angle to the direction and an opening at or near the sloped portion, said sloped portion positioning the outlet end of the capillary column relative to said opening; and a detector for detecting sample components in the eluent from the outlet end, said detector positioned within said alignment device and spaced apart from the outlet end of the capillary column by a gap, said alignment device positioning said detector relative to said opening, thereby aligning said detector with the outlet end.

29. A method of aligning a capillary column with a device for detecting one or more sample components in an eluent from the capillary column, in which there is provided a capillary column having an outlet end from which the eluent exits the capillary column, the outlet end oriented along a direction, and a detector for detecting one or more sample components in the eluent, comprising:

providing an alignment device including a vessel containing an electrolyte, said vessel having a sloped portion at an acute angle to the direction and an opening at or near the sloped portion;

positioning the detector within said alignment device such that the detector is spaced apart from the outlet end of the capillary column by a gap; and causing relative motion between said alignment device and the outlet end of the capillary column, such that the sloped portion positions the outlet end of the capillary column relative to said opening to cause the outlet end of the capillary column to be positioned relative to the detector.

30. The method of claim 29 in which said step of causing relative motion includes causing the outlet end of the capillary column to contact the sloped portion and to move therealong toward the opening.

31. A method of detecting one or more sample components in an eluent from a capillary column during capillary electrophoresis, in which there is provided a capillary column having an outlet end from which an eluent exits the capillary column, the outlet end oriented along a direction, and a detector for detecting one or more sample components in the eluent, comprising:

providing an alignment device including a vessel containing an electrolyte, said vessel having a sloped portion at an acute angle to the direction and an opening at or near the sloped portion, said alignment device dimensioned to allow the eluent to pass by the detector and into said vessel;

positioning the detector within said alignment device;

causing relative motion between said alignment device and the outlet end of the capillary column, such that the sloped portion positions the outlet end of the capillary column relative to said opening to cause the outlet end of the capillary column to be positioned relative to the detector, and such that the outlet end of the capillary column is submerged in the electrolyte;

causing one or more sample components in the eluent to pass by the detector and into said vessel; and detecting one or more sample components as the eluent passes by the detector.

32. The method of claim 31, wherein said positioning step includes positioning the detector such that the detector is spaced apart from the outlet end of the capillary column by a gap.

33. The method of claim 31 in which said step of causing relative motion includes causing the outlet end of the capillary column to contact the sloped portion and to move therealong toward the opening.

34. The method of claim 31, further comprising providing at least one ancillary electrode in electrical communication with the electrolyte, wherein said step of causing the passing by of one or more sample components in the eluent includes applying an electrical field to said ancillary electrode to cause the one or more sample components to pass by the detector and into said vessel.

35. A capillary electrophoresis method, in which there is provided a capillary column including an electrolyte therein and having an inlet and an outlet end from which an eluent exits the capillary column, the outlet end being oriented along a direction, a power source for applying an electrical field between the inlet and the outlet end to cause separation of a sample, and a detector for detecting one or more sample components in the eluent from the outlet end, comprising:

providing an alignment device including a vessel, said vessel containing an electrolyte electrically communicating with the electrolyte in said capillary column and having a sloped portion at an acute angle to the direction and an opening at or near the sloped portion, said alignment device dimensioned to allow the eluent to pass by the detector and into said vessel;

positioning the detector within said alignment device;

causing relative motion between said alignment device and the outlet end of the capillary column, such that the sloped portion positions the outlet end of the capillary column relative to said opening to cause the outlet end of the capillary column to be positioned relative to the detector and such that the outlet end of the capillary column is submerged in the electrolyte in said vessel;

applying an electrical field between the inlet and the outlet end of the capillary column;

causing one or more sample components in the eluent to pass by the detector and into said vessel; and detecting one or more sample components as the eluent passes by the detector.

36. The method of claim 35, wherein said positioning step includes positioning the detector such that the detector is spaced apart from the outlet end of the capillary column by a gap.

37. The method of claim 35 in which said step of causing relative motion includes causing the outlet end of the capillary column to contact the sloped portion and to move therealong toward the opening.

38. The method of claim 35, further comprising providing at least one ancillary electrode in electrical communication with the electrolyte in said vessel, wherein said step of causing the passing by of one or more sample components in the eluent includes applying an electrical force to said ancillary electrode to cause the one or more sample components to pass by the detector and into said vessel.

* * * * *